United States Patent [19]

Hsieh et al.

[11] Patent Number: 5,462,863
[45] Date of Patent: Oct. 31, 1995

[54] ISOLATION OF HEPATITIS B SURFACE ANTIGEN FROM TRANSFORMED YEAST CELLS

[75] Inventors: Jih-Han Hsieh, Parsippany, N.J.; Shu-Ching Shih, York Avenue, N.Y.; Wei-Kuang Chi, Taipei, Taiwan; Yi-Ding Chu, Taipei, Taiwan; Ae-Ning Lin, Taipei, Taiwan

[73] Assignee: Development Center for Biotechnology, Taipei, Taiwan

[21] Appl. No.: 235,029

[22] Filed: Apr. 28, 1994

Related U.S. Application Data

[63] Continuation-in-part of Ser. No. 799,379, Nov. 27, 1991, abandoned, which is a continuation-in-part of Ser. No. 308,441, Feb. 9, 1989, abandoned.

[51] Int. Cl.⁶ .......................... C07K 14/085; C07K 1/30; C07K 1/36; C12N 15/51
[52] U.S. Cl. .................. 435/69.3; 530/350; 530/395; 530/419; 530/420; 530/421; 530/427; 530/806
[58] Field of Search .................. 435/69.3; 530/350, 530/806, 420, 421, 427, 395; 424/89

[56] References Cited

U.S. PATENT DOCUMENTS

| | | | |
|---|---|---|---|
| 3,951,937 | 4/1976 | Vnek et al. | 424/59 |
| 4,024,243 | 5/1977 | McAleer et al. | 424/89 |
| 4,162,192 | 7/1979 | Mizuno et al. | 435/239 |
| 4,335,214 | 6/1982 | Adamowicz et al. | 435/239 |
| 4,624,918 | 11/1986 | Hershberg | 435/69.3 |
| 4,707,542 | 11/1987 | Friedman et al. | 530/371 |

FOREIGN PATENT DOCUMENTS

| | | |
|---|---|---|
| 177015 | 4/1986 | European Pat. Off. . |
| 0179485 | 4/1986 | European Pat. Off. . |
| 0384058 | 8/1990 | European Pat. Off. . |
| 3508965 | 8/1985 | U.S.S.R. . |

OTHER PUBLICATIONS

Hitzeman, et al. (1983) "Expression of Hepatitis B Virus Surface Antigen in Yeast", *Nucleic Acids Research*, 11, 2745–2763.

Kobayashi, et al. (1988) "Recombinant Hepatitis B Virus Surface Antigen Carrying the pre-S2 Region Derived from Yeast", Abstract, DBA Accession No.: 88–10708 from DIALOG file 357, *J. Biotechnol.*, 8, 1–22.

Miyanohara, et al. (1983) "Expression of Hepatitis B Surface Antigen Gene in Yeast", *Proc. Natl. Acad. Sci. USA*, 80, 1–5.

Valenzuela, et al. (1982) "Synthesis and Assembly of Hepatitis B Virus Surface Antigen Particles in Yeast", *Nature*, 298, 347–350.

Jendrisak, J. 1987. Jn R. Burgess (ed.), *Protein Purification: Micro to Macro*, Alan R. Liss, Inc. New York, pp. 75–97.

Bonnerjea et al. 1986. Bio/Technology 4:955,958.

*Primary Examiner*—Keith C. Furman
*Attorney, Agent, or Firm*—Fish & Richardson

[57] ABSTRACT

A method for recovering hepatitis B surface antigen protein from transformed yeast cells including the steps of (i) obtaining an aqueous homogenate of the yeast cells; (ii) enriching the hepatitis B surface antigen protein in the homogenate with a protein-aggregating reagent to form a precipitate which contains hepatitis B surface antigen protein; (iii) dissolving the precipitate in a buffer to form a suspension; and (iv) post-homogenizing the suspension to obtain a 10% to 50% increase in yield of the hepatitis B surface antigen protein as calculated based on a yield achieved without performing the post-homogenizing step.

26 Claims, No Drawings

ISOLATION OF HEPATITIS B SURFACE ANTIGEN FROM TRANSFORMED YEAST CELLS

CROSS REFERENCE TO RELATED APPLICATIONS

This application is a continuation-in-part of U.S. Ser. No. 07/799,379 filed Nov. 27, 1991, now abandoned, which in turn is a continuation-in-part of U.S. Ser. No. 07/308,441 filed Feb. 9, 1989, now abandoned.

BACKGROUND OF THE INVENTION

The present invention is related to a method for isolating hepatitis B surface antigen (or "HBsAg") from transformed yeast cells.

It is known that hepatitis B surface antigen protein can be purified from infected human plasma and used as a vaccine to prevent hepatitis B virus infection. HBsAg genes have been cloned and expressed in *E. coli*, yeast cells and mammalian cells to reduce the dependency on plasma. The synthesis of HBsAg recovered as 22 nm particles in yeast cells, e.g. *Saccharomyces cerevisiae*, has been reported by Valenzuela et al., *Nature*, 298:347–350 (1982); by Hitzeman et al., *Nucleic Acid Research*, 11:2745–2763 (1983) and by Miyanohara et al., *Proc. Nat'l Acad. Sci.*, 80:1–5 (1983).

Recombinant HBsAg protein particles produced by transformed *Saccharomyces cerevisiae* (Baker's yeast) have been isolated as described in U.S. Pat. No. 4,707,542. Normally, the expressed HBsAg was separated and purified from cell homogenate via the addition of protease inhibitor of phenylmethylsulfonylfluoride (PMSF) and non-ionic detergent polyoxyethylene (9,5)-p-t-octyl-phenol (Triton® X-100) to the cell homogenate. Then, chaotropic agents such as potassium or sodium thiocyanate (KSCN or NaSCN) or urea, can be used to formulate different forms of surface antigen protein aggregates followed by adsorption onto fused silica, borate N-morpholine propanesulfonic acid (MOPS) buffer elution, hydrophobic interaction chromatography on butyl agarose, treatment with polystyrene beads cross-linked with divinylbenzene (Amberlite XAD-2 resin), ultrafiltration, sepharose 6B chromatography, as well as immunoaffinity and ECTHAM-cellulose chromatography purification steps.

An improvement on the hydrophobic interaction chromatography using various hydrophobic groups as the fixing carrier was reported in European Patent publication No. 0179485A2. Also, U.S. Pat. No. 4,624,918 described a method for the purification of HBsAg from recombinant cell culture via concentration, precipitation, immunoaffinity column, anion exchange and gel permeation chromatography.

SUMMARY OF THE INVENTION

An object of the present invention is to provide an improved method for the separation and recovery of HBsAg protein particles from transformed yeast cells. More specifically, the present invention provides a method for increasing recovery of HBsAg protein From transformed yeast cells.

A further object of the present invention is to provide a method for extracting HBsAg from cell homogenate without the addition of inhibitors or detergents.

A still another object of the present invention is to provide a faster and more economical method for efficient recovery of HBsAg particles in high purity.

In accordance with the present invention, it has been discovered that HBsAg protein particles produced by transformed yeast cells can be selectively recovered from cell homogenate with high yield by the use of selective polyethylene glycol ("PEG") precipitation and post-homogenization (to be defined below). The PEG used can be easily removed by diafiltration and zonal ultracentrifugation. Post-homogenization not only facilitates mixing and simplifies downstream processing, it also enhance the recovery yield of the HBsAg protein. Highly purified HBsAg protein particles can be obtained by further purification.

In particular, an embodiment of this invention features a method for recovering hepatitis B surface antigen protein from transformed yeast cells comprising the steps of (i) obtaining an aqueous homogenate of the yeast cells; (ii) enriching the hepatitis B surface antigen protein in the homogenate with a protein-aggregating reagent to form a precipitate which contains hepatitis B surface antigen protein; (iii) dissolving the precipitate in a buffer to form a suspension; and (iv) post-homogenizing the suspension to obtain a 10% to 50% or 20% to 40% increase in yield of the hepatitis B surface antigen protein. The increase in yield is calculated based on a yield achieved without performing the post-homogenizing step. The yields are determined by either of the two immunoassays conducted in Examples 1–4 below.

Refer to step (i) first. The yeast cell homogenate can be obtained by breaking and homogenizing transformed yeast cells following various procedures which are within the capability of a person of ordinary skill in the relevant art.

One of the protein-aggregating reagents which can be used to practice the enriching step described above, i.e., step (ii), is PEG. Preferably, PEG-6000 (i.e., MW 6,000) is used at a final concentration of 8% by weight (i.e., 8% by weight of the HBsAg-containing solution to be enriched, or 8% w/w with w/w referring to the weight of PEG to that of the solution to be enriched). Ammonium sulfate can also be used as the protein-aggregating reagent at a final concentration of 45% to 60% saturation.

In step (iii), the precipitate can be dissolved (or, more precisely, dispersed) in a buffer (a preferred weight to weight ratio varies from ⅙ to ½, with the particularly preferred ratio being ⅓) to form a suspension by stirring the precipitate-buffer mixture with a magnetic stirrer, by manually stirring it with a spatula, or by any analogous stirring or shaking operation. The term "dissolve" herein refers to any such operation which is thoroughly performed.

The term "post-homogenization" or "post-homogenizing," on the other hand, refers to the process of homogenizing a HBsAg-precipitate obtained via the use of a protein-aggregating reagent, as distinguished from the process of homogenizing transformed yeast cells. As an example, the post-homogenizing step, i.e., step (iv), can be achieved by using a POLYTRON homogenizer (Kinematica AG, Littau/Lucerne, Switzerland) or its equivalent, i.e., by inserting a rod into the suspension and rotating it at 1,000 rpm to 30,000 rpm (preferably, 2,000 rpm to 8,000 rpm), the rod being disposed within a stationary sleeve. As another example, post-homogenization can also be achieved by subjecting the suspension to a pressure of 5,000 psi to 20,000 psi (preferably, 8,000 psi to 17,000 psi) using a high pressure homogenizer such as a MICROFLUIDIZER M-110T (Microfluidics Corp., Newton, Mass.), an APV Gaulin homogenizer LAB 60 (APV Gaulin, Inc., Wilmington, Mass.) or an equivalent thereof. Alternatively, one can wet-mill the suspension with beads having diameters of 0.1 mm to 2 mm (preferably, 0.2 mm to 1 mm) for a residence time of 30 seconds to 30 minutes (preferably, 1 minute to 10 minutes) employing a bead milling machine such as DynoMill KD L, KD5 or its equivalent (Willy A. Bachofen, Engineering Works, Basel, Switzerland).

Preferably, the method of this invention described above further comprises the step of removing cell debris in the aqueous cell homogenate before performing the enriching step, i.e., step (ii), either by centrifugation or by filtration.

Additional or varied conditions for performing the above method can be determined by a skilled person in the art. As an example, acceptable temperatures are those at which HBsAg protein does not undergo denaturation (e.g., ranging from above 0° C. to 40° C.). As another example, high pressure post-homogenization can be repeated on the same suspension for thoroughness, if necessary. Similarly, when a POLYTRON homogenizer or its equivalent is used, the operation time depends on factors such as the volume of the suspension, the rotation rate of the rod, or the like, and can be readily determined by a skilled person in the art.

Other features and advantages of the present invention will be apparent from the following description of the preferred embodiments, and also from the appending claims.

DESCRIPTION OF THE PREFERRED EMBODIMENTS

An embodiment of the present invention relates to a method for isolating hepatitis B surface antigen from transformed yeast cells which comprises:

(a) breaking and homogenizing the cells to give a cell homogenate;

(b) recovering the Hepatitis B surface antigen protein by at least one cycle comprising precipitation with from 1 to 10 weight percent polyethylene glycol followed by post-homogenization; and (c) further purifying the HBsAg protein.

Recombinant hepatitis B surface antigen protein particles are synthesized by transformed yeast cells, especially *Saccharomyces cerevisiae*. The yeast cells are transformed by the recombinant genes plasmid containing DNA molecules coding for HBsAg protein and cultured in a fermentation medium under suitable conditions. The HBsAg genes can be constitutively expressed in the yeast cells.

The expressed yeast cells are repeatedly washed and centrifuged to remove entrained fermentation medium components. The cells are suspended in tris buffer solution in the presence or absence of a detergent such as polyoxyethylene (9,5)p-t-octylphenol (Triton® X-100). Usually, the cells must be suspended in the buffer containing a detergent to enhance the separation of protein; however, the method according to the present invention can be carried out in the absence of detergent.

The cell suspension is preferably adjusted to an optical density of about 250 to 350 at 600 nm and then pumped into a glass-bead homogenizer such as Dyno-Mill at an optimum flow rate and glass bead concentration to ensure maximum breakage of the cells. A cell homogenate is thus obtained.

The cell homogenate thus obtained is centrifuged. The cell supernatant is then subjected to selective precipitation and post-homogenization. The selective precipitation is carried out by sequentially adding from about 1 to 10% w/w of PEG having a molecular weight of about 2,000 to 10,000, preferably 6,000 (w/w refers to the weight of PEG to that of the cell supernatant). As an example, the post-homogenization can be carried out with a POLYTRON cell homogenizer (e.g., at 2,000–6,000 rpm for 10–60 seconds at 0°–10° C.).

A scheme comprises adding 3% w/w of PEG to the cell supernatant to precipitate cellular proteins and, after centrifugation, adding 8% w/w of PEG to the supernatant of the first precipitation. The resulting precipitate is then subjected to post-homogenization. E.g., see Example 1 below.

Another scheme comprises adding 8% w/w of PEG to the cell supernatant to precipitate HBsAg, and, after centrifugation, subjecting the precipitate to post-homogenization. This step is followed by addition of 3% w/w of PEG to the post-homogenized pellet suspension, centrifugation, and addition of 8% w/w of PEG to the second PEG treated supernatant. The resulting precipitate is subjected to post-homogenization. E.g., see Example 2 below.

Experiments similar to those described in Examples 1 and 2 below show that the sequential addition of PEG facilitates the removal of cellular proteins and improves the recovery of HBsAg. The sequential precipitation results in about 150 to 200 folds of purification over usual methods. The effect of the sequential precipitation on the recovery of HBsAg is shown in Tables 1-1 and 1-2.

Table 1-1 shows the optimum HBsAg recovery is obtained by the addition of 8% w/w of PEG, but the level of the undesired protein is also very high.

TABLE 1-1

Recovery of HBsAg by Single Step Precipitation with Polyethyleneglycol - 6000 (PEG-6000)

| | PEG % | | | | |
| --- | --- | --- | --- | --- | --- |
| | 1% | 2% | 3% | 4% | 8% |
| HBsAg Recovery (%) | 3.9 | 10.3 | 17.1 | 21.2 | 86.5 |
| Undesired Protein (%) | 7.5 | 16.9 | 34.0 | 35.0 | 46.7 |

When HBsAg is recovered by double-step precipitation, the recovery of undesired protein is decreased (shown in Table 1-2). Therefore, the optimum HBsAg recovery is obtained by the procedure comprising the addition of 3% followed by 8% PEG precipitation.

TABLE 1-2

Recovery of HBsAg by Double Step Precipitation with Polyethyleneglycol-6000 (PEG-6000)

| | PEG % | | |
| --- | --- | --- | --- |
| | 1% + 8% | 2% + 8% | 3% + 8% |
| HBsAg Recovery (%) | 86.3 | 85.1 | 83.2 |
| Undesired Protein (%) | 38.6 | 27.1 | 15.3 |

The post-homogenization step also enhances the recovery of HBsAg. The recovery obtained by the post-homogenization (shown in Table 2) suggests that the HBsAg protein synthesis and protein particle formation in the yeast cells are in the organelle such as endoplasmic reticulum. The post-homogenization facilitates the release of HBsAg particles from precipitated endoplasmic reticulum or microsome.

TABLE 2

Enhanced HBsAg Recovery by Post-Homogenization

| Run No. | Before* | Pellet/Buffer§ | After*† |
| --- | --- | --- | --- |
| 1 | 82.8% | 1/5 | 102.3% (24%) |
| 2 | 89.6% | 1/4 | 117.8% (31%) |

TABLE 2-continued

Enhanced HBsAg Recovery by Post-Homogenization

| Run No. | Before* | Pellet/Buffer§ | After*† |
| --- | --- | --- | --- |
| 3 | 88.5% | 1/3 | 130.5% (47%) |

*The yields obtained before and after post-homogenization, respectively
§weight to weight ratio
†Numbers in the parentheses are increases in yield from post-homogenization Note that some of the yields shown in Table 2 of the specification were higher than 100%, which can be explained as follows. Naturally occurring HBsAg is an aggregated ~20 nm-protein particle which consists of about 100 monomers (M.W. 23,000). Thus, plasma-derived HBsAg prepared from a hepatitis B carrier is a stable aggregated particle. By contrast, yeast-derived HBsAg also contains monomers, dimers and the like, more of which assemble into aggregated particles during the purification process. Therefore, yeast-derived HBsAg molecules have different conformational compositions (monomers, dimers, . . . , and particles) along the purification process. See Heermann et al., *J. of Virology* 52.:396 (1984); and Hitzeman et al., *Nucleic Acid Res.* 11:2745 (1983). The HBsAg particle is about 1000-fold more immunogenic than the unassembled HBsAg protein. See Valenzuela et al., *Nature* 298:347 (1982). As a matter of fact, the antibody provided in Abbott's Radioimmunoassay kits (see Examples 1–3 below), which were used by Applicants to monitor the recovery of HBsAg, only reacts with HBsAg particles, but not with HBsAg monomers. See Araki, et al., *Gene* 89:195 (1990). Thus, the greater than 100% yields from the use of a Polytron homogenizer as shown in Table 2 of the specification clearly are believed to be the result of the changes in conformational compositions during the purification processes. In other words, although the mass of HBsAg decreased along the purification process, the content of the immunogenic particles (e.g., % by weight) increased. As a net result, greater than 100% yields were shown using the HBsAg particle-specific immunoassay. Note that a particle-specific immunoassay was used since only particles, which are far more immunogenic than the unassembled HBsAg protein, are useful for the preparation of vaccines.

The HBsAg protein particles are partially purified by the above procedures. Further purification steps include sucrose gradient ultracentrifugation and CsCl gradient ultracentrifugation, process scale continuous zonal ultracentrifugation, size exclusion chromatography and stepwise CsCl gradient ultracentrifugation. The purified HBsAg particles have the same physical and chemical characteristics as those derived from human plasma.

The following examples are offered to aid in understanding of the present invention and are not to be construed as limiting the scope thereof. Unless otherwise indicated, all parts and percentages are by weight.

A third scheme does not involve sequential additions of PEG and comprises adding 8% w/w of PEG to the cell supernatant to precipitate HBsAg, and, after centrifugation, subjecting the precipitate to post-homogenization. This step is followed directly by further purification without using PEG or any other protein-aggregating reagent. E.g., see Examples 3 and 4 below.

Below is a more thorough discussion of post-homogenization of a HBsAg-containing suspension and precipitation of HBsAg protein using a protein-aggregating reagent.

At least three types of devices can be used to perform the post-homogenization, namely, a POLYTRON homogenizer or its equivalent, a high pressure homogenizer or its equivalent, and a bead mill or its equivalent.

A POLYTRON homogenizer includes a rotatable steel rod disposed within a stationary steel sleeve. The distance between the rod and the sleeve may vary and are typically 0.1 to 0.5 mm. Rotation of the rod at a high speed causes particulate material in the suspension to be processed to impinge on the surface of the rod and/or the sleeve, thereby resulting in homogenization. For more structural details of a POLYTRON homogenizer, see PT-K/PT-G 4/92 (a brochure published by Kinematica AG), which is hereby incorporated by reference.

The APV Gaulin High Pressure Homogenizer LAB 60 or its equivalent in principle operates as follows. A positive displacement piston pump with one or more plungers delivers the cell suspension into a valve assembly. When the highly pressurized liquid enters the valve, at the present pressure a rapid change of velocity occurs, accompanied by a rapid pressure drop down to the vapor pressure of the liquid. During discharge the suspension passes between the valve and its set and impinges on the impact ring. The magnitude of the pressure drop is one of the mechanisms contributing to the high shear forces occurring during the high acceleration of the liquid in the gap and impingement stress taking place at the valve and impact ring play a part.

Another high pressure homogenizer, MICROFLUIDIZER M-110T or its equivalent, on the other hand, operates by orienting the liquid stream in precisely defined microchannels and impinging them against one another. Oscillation of the cell liquid, due to turbulent eddies, is another explanation for why the homogenization effect occurs.

An example of a wet milling machine is DynoMill KD L, KD 5 or its equivalent. The chamber of such a machine is filled with glass beads. Homogenization is brought about by shear generated by the differential velocity of streaming layers of glass beads at a high agitator speed. An agitator tip speed of 500 rpm to 1000 rpm (preferably, 1,500 rpm to 5,000 rpm) and a residence time of 30 seconds to 30 minutes (preferably, 1 minute to 10 minutes) can be used.

For a thorough discussion of various types of homogenizers, see Schutte et al., *Biotech. & App. Biochem.*, 12:599–620 (1990), which is hereby incorporated by reference.

There are various methods for preferentially precipitating a given protein. See Chap. 3 "Separation by Precipitation" in Scopes, Protein Purification—Principle and Practice, 2nd Ed., Springer-Verlag (1987) and Section VI. "Purification Procedures: Bulk Methods" in Methods in Enzymology, Vol. 182, Guide to Protein Purification, Ed. Deutscher, Academic Press Inc. (1990), both of which are hereby incorporated by reference.

More specifically, methods of precipitation includes:

A. salt

Proteins can be precipitated by adding high concentrations of inorganic salts. The solvation of salt ions pulls off water molecules from the hydrophobic side chains of protein. The exposed hydrophobic areas interact with each other to form aggregates. Ammonium sulfate is commonly used to salt out certain proteins, including HBsAg. See U.S. Pat. Nos. 4,612,283 and 4,624,918, both of which are hereby incorporated by reference. As discussed in these two patents, ammonium sulfate with a concentration range of 45 to 60% saturation can be used to precipitate HBsAg.

B. pH

The solubility of protein normally reaches a minimum value at its isoelectric point. Adjustment of pH can be used to precipitate the desired protein or to remove contaminating protein while keeping the desired product in solution.

C. organic solvent

Water-miscible organic solvents such as ethanol, methanol, isopropanol, or acetone can be used to precipitate proteins by lowering the dielectric constant of the medium and therefore increasing intermolecular electrostatic interactions.

D. nonionic polymer

Hydrophilic polymers, such as PEG, have been used as protein precipitating agents. The polymer may extrude proteins from part of the solution thereby promoting protein-protein interactions.

E. polyelectrolyte

Networks of polyelectrolytes (e.g., polyethyleneimine) and proteins can be formed and this causes the flocculation effect. Because electrostatic interaction is involved, the basic proteins are usually precipitated at a lower pH with anionic polymers such as polyacrylates while acidic proteins might act at a higher pH with positively charged polymers such as DEAE-dextran.

F. polyvalent metal ion

A number of polyvalent metals are effective in precipitating proteins. They may bind to carboxylic acids ($Ca^{2+}$, $Ba^{2+}$, $Zn^{2+}$), both carboxylic acids and nitrogenous compounds ($Mn^{2+}$, $Fe^{3+}$, $Co^{2+}$, $Ni^{2+}$, etc.), or simply sulphydryl groups ($Ag^{+}$, $Hg^{2+}$, $Pb^{2+}$) in proteins.

G. temperature

Heating can be used to selectively denature and recover the desired protein or to remove unwanted products.

H. affinity

Specific ligands such as antibodies or bifunctional ligands can be used to precipitate proteins from solution by forming one-dimensional, two-dimensional or three dimensional complex.

Without further elaboration, it is believed that one skilled in the art can, based on the description above, utilize the present invention to its fullest extent. The following specific embodiments are, therefore, to be construed as merely illustrative, and not limitative of the remainder of the disclosure in any way whatsoever.

EXAMPLE 1

Sixty liters of the fermentation broth of the transformed *Saccharomyces cerevisiae* yeast cells were subjected to batch centrifugation in a Beckman J2-21 centrifuge at 9000 g force (8000 rpm) for 5 minutes using a JA-10 rotor (3 liters capacity per batch), and then 6250 grams wet weight (or approximately 1560 grams dry weight) of the cells were harvested. The cell pellet from the centrifuge tube was suspended in TBS 1 buffer solution (10 mM Tris-HCl Tris<hydroxymethyl>aminomethane pH 7.5, 0.14M NaCl) and repelleted to remove entrained fermentation medium components. The pelleted yeast cells were resuspended in TBS 2 buffer solution (10 mM Tris-HCl pH 7.5, 0.5M NaCl, 0.1% Triton® X-100) to a final optical density at 660 nm ($OD_{660}$) of 300 and then the cell suspension was pumped into a homogenizer (Dyno-Mill, Willy, Model KDL) at a flow rate of 70 ml/min with a peristaltic pump. 19,100 grams of cell homogenate were obtained and centrifuged at 12,000 g force (9000 rpm) for 15 min in the J2-21 centrifuge, resulting in a total of 15,400 grams of supernatant. The hepatitis B surface antigen concentration in the supernatant was 10 mg/l as measured by the AUSRIA method (Abbott Radio-immuno Assay) and the total protein concentration analyzed by the well known Lowry method was 28 g/l. For details of the AUSRIA method, see AUSRIA II-125 Antibody to Hepatitis B Surface Antigen $^{125}I$ (Human), Abbott Laboratories, Diagnostic Division, North Chicago, Ill. (October, 1985, 83-0981/R12), which is hereby incorporated by reference.

Polyethylene glycol solution (50% PEG-6000, which has a molecular weight of 6,000) was added to the supernatant at a rate of 150 g/min to a final concentration of 8% w/w to precipitate HBsAg while stirring at 4° C. for 16 hours. After centrifugation at 12,000 g for 15 minutes, the 1,365 grams of precipitated material were dissolved in TBS 1 with three times the original weight and then the suspension was homogenized with a POLYTRON homogenizer (Kinematica AG, Switzerland; controller: PT-K/PCU-11, aggregate: PTA 10S) at 4,500 rpm for 30 seconds, three times at 4° C. (less than 300 ml in a 500 ml-centrifuge bottle). The homogenate was treated with PEG-6000 to a final concentration of 3% w/w to precipitate yeast cellular proteins at 4° C. for 6 hours. The precipitated protein was removed by centrifugation at 12,000 g (9000 rpm) for 15 minutes. The resulting supernatant was again treated with PEG-6000 to a final concentration of 8% w/w to precipitate HBsAg while stirring at 4° C. for 16 hours. The second precipitation was obtained by centrifugation at 12,000 g for 15 minutes. The supernatant was removed and the pellet (approximately 455 grams) was dissolved in TBS 1 with three times the weight and then homogenized by the same Polytron homogenizer. The protein suspension was then filtered through 0.22 micron porous membrane. The filtrate was harvested by continuously washing the membrane with TBS 1. The membrane with molecular weight cut off (MWCO) 100,000 (Millipore Pellicon Unit) was used for ultrafiltration to concentrate the filtrate. The retentate was collected (about 2,000 grams).

The retentate was subjected to further treatment to purify HBsAg from yeast cellular proteins. The separation was performed by differential sedimentation through centrifugation. 1,800 ml of 40% sucrose solution and 1,400 ml of TBS 1 solution were loaded into an ENI (Electro-Nucleonic Inc., K-3 core) ultracentrifuge using a peristaltic pump. Two liters of sample were fed into the bottom of the rotor at a constant rate of 10 liters per hour. A sucrose gradient of 2 to 40 percent was formed by dynamic re-orientation of the centrifuge at 35,000 rpm (90,000 g) at 4° C. The fractions were collected with 200 ml per fraction after 3 hours of operation.

Fractions were selected by detection of HAU (Hemagglutination Unit), $OD_{280}$ and refractive index, and pooled together, followed by the utilization of ultrafiltration membranes with molecular weight cutoff of 100,000 for concentration and diafiltration to remove sucrose. The resulted solution was adjusted to a volume to 800 ml.

The separation of HBsAg particles was performed by cesium chloride (CsCl) gradient ultracentrifugation with densities ranging from 1.10 to 1.25 g/cm$^3$. Fractions were selected and concentrated by diafiltration and ultrafiltration (to about 100 ml). Further purification of the HBsAg protein particles from yeast proteins was carried out by size exclusion chromatography (TSK HW-65). The selected fractions were pooled together and subjected to a step-wise CsCl gradient ultracentrifugation in Beckman zonal rotor (type Ti-15), using the CsCl stepped solutions: a density of 1.30, 1.25, 1.20, 1.10 and starting from 1.15. After ultracentrifugation at 31,000 rpm (100,000 g), 4° C. for 44 hours, the selected HBsAg fractions were dialyzed to remove CsCl and concentrated by ultrafiltration to obtain further purified HBsAg protein particles.

EXAMPLE 2

The fermentation yeast cells were harvested and broken according to the procedures as described in Example 1. After centrifugation (12,000 g, 15 min) to remove yeast cell debris, PEG-6000 was added to the supernatant to reach a final concentration of 3% w/w and the resulting solution was stirred at 4° C. for 6 hours and then centrifuged at 4° C. (12,000 g, 15 min) to remove the precipitate. PEG-6000 solution (50%) was added to the supernatant to reach a final concentration of 8% w/w while stirring at 4° C. for 16 hours. After centrifugation, the precipitate was subjected to a post-homogenization using the same Polytron homogenizer at 4° C. (4,500 rpm, 30 seconds). The homogenate was then purified according to the procedures described in Example 1 to obtain the purified HBsAg protein particles.

EXAMPLE 3

One hundred liters of fermentation broth of transformed *Saccharomyces cerevisiae* yeast cells were filtered through 0.45 μm membrane in a Millipore Prostak system to harvest and wash the cells. TBS2N buffer solution (25 mM Tris base, 0.5M NaCl, pH 7.2) was used in cell wash and a cell suspension of 30 liters was obtained. Triton X-100 (25%) was added to the cell suspension to a concentration of 0.1% (v/v) and the suspension was stirred for 30 minutes. Then the cell suspension was homogenized in a Dyno-Mill (Willy, Model KD5) at a flow rate of 400 g/min to break up the cells.

Thirty two liters of cell homogenate were obtained and centrifuged at 600 g/min in a Westfalia CSA-8 centrifuge and a supernatant of 26,000 grams was obtained. XAD-2 resin was added to the supernatant to remove Triton X-100. The weight ratio of supernatant to XAD-2 resin was 30:1. The suspension was stirred at 4° C. for 30 minutes and then filtered through at 80 mesh filter to remove the XAD-2 resin. The 25,300 grams filtrate thus obtained was frozen for 54 hours at −20° C. and thawed for 10 hours at 4° C. Ten kilo grams of the thawed filtrate (only part of the filtrate was used) was centrifuged in a Beckman J2-21 centrifuge using JA-10 rotor at 9,000 g for 30 minutes.

Polyethylene glycol solution (50%) having molecular weight of 6000 (PEG-6000) was added to the supernatant at a rate of 200 g/min to a final concentration of 8% (w/w) to precipitate HBsAg while stirring at 4° C. for 2 hours. The suspension was centrifuged in Beckman J2-21 centrifuge using JA-10 rotor at 9,000 g for 15 minutes. The precipitate was recovered and resuspended in TBS1 buffer solution (10 mM Tris base, 0.15M NaCl, pH 7.5). The weight of buffer was three times the weight of the precipitate.

A 1,472-gram suspension thus obtained was thoroughly dissolved by stirring at room temperature in a 5 liter beaker using a magnetic stirrer (Model Nuova II, Thermolyne, Dubuque, Iowa) for 2 hours. The stir bar used was 3"×½" and the speed of stirring was set at scale 8 (full scale being 10), resulting in a vortex which was about ½ depth of the solution. [Note that, as a routine process, in numerous experiments the pellet suspension was stirred magnetically overnight (18 hours) at 4° C. after stirring at room temperature for 2 hours. The yield of HBsAg was in range of 90–100%, with the yield of the pre-PEG precipitation supernatant being set as 100%. Thus, the degree of the dissolution achieved in this working example (i.e., 95% HBsAg yield, see Table 3 below) was consistent with that obtained from the routine process.]

A 100 ml-aliquot of the dissolved suspension was then homogenized in a 500 ml-centrifuge bottle using a Polytron homogenizer (Kinematica AG, Model PT-K, Switzerland; controller: PT-K/PCU-11, aggregate: PTA 10S) at 4,500 rpm for 30 seconds, 3 times.

The post-homogenization operation using a Polytron homogenizer increased the yield of HBsAg by 40% as shown in the following table. The yields of HBsAg were determined using an immunoassay kit, AUSZYME MONOCLONAL, provided by Abbott Laboratories. For procedures and other information, see Antibody to Hepatitis B Surface Protein Antigen (Mouse Monoclonal): Peroxidase (Horseradish) Conjugate, Abbott Laboratories, List No. 1980 (February, 1990), which is hereby incorporated by reference.

TABLE 3

| Effect of POLYTRON Homogenization on the recovery of HBsAg | |
|---|---|
| sample | HBsAg yield (%) |
| supernatant (before PEG precipitation) | 100.0* |
| PEG pellet suspension (after stirring) | 94.6 |
| after POLYTRON | 132.4 (40%)† |

*set as 100.0% for comparison with yields from subsequent steps
†the increase calculated based on the yield without post-homogenization

EXAMPLE 4

A 400 ml-aliquot of the dissolved suspension obtained as described in Example 3 was homogenized using a MICROFLUIDIZER homogenizer (Microfluidics, Model M-110T) at 15,000 psi, 2 passes with a flow rate of 300 ml/min.

The post-homogenization operation using a Microfluidizer homogenizer increased the yield of HBsAg by 41% as shown in the following table.

TABLE 4

| Effect of MICROFLUIDIZER Homogenization on the recovery of HBsAg | |
|---|---|
| sample | HBsAg yield (%) |
| supernatant (before PEG precipitation) | 100.0* |
| PEG pellet suspension (after stirring) | 94.6 |
| after MICROFLUIDIZER | 133.0 (41%)† |

*set as 100.0% for comparison with yields from subsequent steps
†the increase calculated based on the yield without post-homogenization

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for recovering hepatitis B surface antigen protein from transformed yeast cells comprising the steps of:

obtaining an aqueous homogenate of said yeast cells;

enriching said hepatitis B surface antigen protein in said homogenate with a protein-aggregating reagent to form a precipitate which contains hepatitis B surface antigen protein;

dissolving said precipitate in a buffer to form a suspension; and post-homogenizing said suspension to obtain a 10% to 50% increase in yield of said hepatitis B surface antigen protein; wherein said 10% to 50% increase in yield is calculated based on a yield achieved without performing said post-homogenizing step.

2. The method of claim 1, wherein said post-homogenizing step comprises inserting a rod into said suspension and rotating said rod at 1,000 rpm to 30,000 rpm, said rod being disposed within a stationary sleeve.

3. The method of claim 2, wherein said rod is rotated at 2,000 rpm to 8,000 rpm.

4. The method of claim 2, wherein said increase in yield is 20% to 40%.

5. The method of claim 1, wherein said post-homogenizing step comprises subjecting said suspension to a pressure of 5,000 psi to 20,000 psi.

6. The method of claim 5, wherein said pressure is 8,000 psi to 17,000 psi.

7. The method of claim 5, wherein said increase in yield is 20% to 40%.

8. The method of claim 1, wherein said post-homogenizing step comprises milling said suspension with beads having diameters of 0.1 mm to 2 mm for 30 seconds to 30 minutes.

9. The method of claim 8, wherein said suspension is milled with beads having diameters of 0.2 mm to 1 mm for 1 minute to 10 minutes.

10. The method of claim 8, wherein said increase in yield is 20% to 40%.

11. The method of claim 1, wherein said precipitate is formed with polyethylene glycol as the protein-aggregating reagent.

12. The method of claim 11, wherein said increase in yield is 20% to 40%.

13. The method of claim 11, wherein said precipitate is formed with polyethylene glycol having a molecular weight of 6,000 daltons as the protein-aggregating reagent at a final concentration of 8% by weight.

14. The method of claim 13, wherein said increase in yield is 20% to 40%.

15. The method of claim 1, wherein said precipitate is formed with ammonium sulfate as the protein-aggregating reagent at a final concentration of 45% to 60% saturation.

16. The method of claim 15, wherein said increase in yield is 20% to 40%.

17. The method of claim 1, wherein said suspension is formed with a weight to weight ratio of said precipitate to said buffer being 1/6 to 1/2.

18. The method of claim 17, wherein said increase in yield is 20% to 40%.

19. The method of claim 16, wherein said ratio is 1/3.

20. The method of claim 19, wherein said increase in yield is 20% to 40%.

21. The method of claim 1, further comprising removing cell debris in said homogenate before performing the enriching step.

22. The method of claim 21, wherein said increase in yield is 20% to 40%.

23. The method of claim 22, wherein said post-homogenizing step comprises inserting a rod into said suspension and rotating said rod at 1,000 rpm to 30,000 rpm, said rod being disposed within a stationary sleeve.

24. The method of claim 22, wherein said post-homogenizing step comprises subjecting said suspension to a pressure of 5,000 psi to 20,000 psi.

25. The method of claim 22, wherein said post-homogenizing step comprises milling said suspension with beads having diameters of 0.1 mm to 2 mm for 30 seconds to 30 minutes.

26. The method of claim 1, wherein said increase in yield is 20% to 40%.

* * * * *